United States Patent [19]

Hu et al.

[11] Patent Number: 4,795,822
[45] Date of Patent: Jan. 3, 1989

[54] NORTRIPTYLINE CONJUGATES TO ANTIGENIC PROTEINS AND ENZYMES

[75] Inventors: Mae W. Hu, Los Altos Hills; Prithipal Singh, Sunnyvale, both of Calif.

[73] Assignee: Syntex (U.S.A.) Inc., Palo Alto, Calif.

[21] Appl. No.: 613,709

[22] Filed: May 23, 1984

[51] Int. Cl.$^4$ .................. C07C 149/40; C07C 149/23
[52] U.S. Cl. ......................................... 560/10; 435/7; 564/192
[58] Field of Search ............... 564/192, 377, 349, 380; 560/10

[56] References Cited

U.S. PATENT DOCUMENTS

| | | | |
|---|---|---|---|
| 2,412,700 | 12/1946 | Weissberger et al. | 564/192 X |
| 3,372,196 | 3/1968 | Engelhardt | 564/377 X |
| 4,223,013 | 9/1980 | Hu et al. | 424/85 |
| 4,241,177 | 12/1980 | Singh et al. | 564/349 X |
| 4,307,245 | 12/1981 | Hu et al. | 564/380 X |
| 4,329,502 | 5/1982 | Singh et al. | 564/349 |

FOREIGN PATENT DOCUMENTS

| | | | |
|---|---|---|---|
| 890423 | 11/1968 | Canada | 260/237.6 |
| 875549 | 12/1968 | Canada | 260/237.6 |
| 0107134 | 8/1983 | European Pat. Off. | 33/54 |
| 1368709 | 6/1964 | France . | |

*Primary Examiner*—Robert V. Hines
*Attorney, Agent, or Firm*—Theodore J. Leitereg

[57] ABSTRACT

Nortriptyline functionalized compounds are provided for conjugation to antigenic compositions, particularly poly(amino acids), and enzymes. The antigenic conjugates are employed for the production of antibodies, which find use in immunoassays for the determination of nortriptyline in a sample, while the enzyme conjugates find use in an enzyme assay for the determination of nortriptyline in a sample.

2 Claims, No Drawings

NORTRIPTYLINE CONJUGATES TO ANTIGENIC PROTEINS AND ENZYMES

BACKGROUND OF THE INVENTION

1. Field of the Invention

Nortriptyline is a tricyclic antidepressant which finds extensive use. The therapeutic range for the drug is from about 50 to 175 ng/ml. Lower dosages do not have significant effect and overdosages have substantial side effects which can be life-threatening. Overdoses can result in convulsions, coma, cardiac arrhythmias, and anticholinergic signs, such as mydriasis and tachycardia.

It is found that the rate of metabolism of the drug can vary widely with individuals, as well as the sensitivity of the individual to the drug. It is therefore necessary to insure proper dosage levels to monitor the plasma level, so that a therapeutic dosage level may be maintained.

In monitoring the dosage level, it is desirable that there be a simple, accurate, rapid technique for measuring the nortriptyline level, which can distinguish nortriptyline from other drugs and metabolites of nortriptyline, which might otherwise give an erroneous value of the nortriptyline level.

2. Brief Description of the Prior Art

Nortriptyline is closely related chemically to amitriptyline. Techniques reported for the determination of amitriptyline in biological fluids include the use of thin-layer chromatography, gas-liquid chromatography (GLC) and GLC-mass spectrometry. Gifford, et al., *J. Chrom.*, 105: 107–113 (1975); Gupta, et al., *Clin. Biochem.*, 9: 247–51 (1976); Nyberg and Martensson, *J. Chromatography*, 143: 491 (1977); Watson and Stewart, *J. Chrom.*, 134: 182 (1977); ibid. 132: 155–159 (1977). Radioimmunoassay has been reported for amitriptyline by Aherne, et al., *Br. J. Clin. Pharmac.*, 3: 561 (1976), Turner, *Lancet*, 1316 (1977); and Aherne, et al., *Lancet* 1214 (1977). In Aherne, et al., ibid., a synthesis for an antigen for antibody formation is described, where nortriptyline was substituted with aminobutylene followed by conjugation to bovine serum albumin employing carbodiimide. In another antigen conjugates synthesis by Kaul, et al., *J. Anal. Tox.*, 1: 236 (1977), nortriptyline was conjugated to bovine serum albumin through a succinic group. The resulting antibodies were found to have significant cross-reactivity with a number of other tricyclic drugs.

U.S. Pat. No. 4,275,160 discloses imipramine derivatives and poly(amino acid) conjugates. U.S. Pat. No. 4,307,245 describes amitripylyine conjugates to antigenic proteins and enzymes. U.S. Pat. No. 4,220,722 discloses a method for conjugating to polyamino compounds employing haloacyl groups and compositions prepared thereby. U.S. Pat. No. 3,458,578 discloses 4-amino-10,11-dihydro-5H-dibenzo[a,d]cyclohepten-5-one. U.S. Pat. No. 3,803,234 generically discloses 2- and 3-nitro-10,11-dihydro-5H-dibenzo[a,d]cyclohepten-5-one.

SUMMARY OF THE INVENTION

A synthetic procedure is provided for preparing nortriptyline derivatives functionalized at the 3-position for conjugation to proteinaceous materials, particularly antigenic and enzymatic poly(amino acids). the antigenic conjugate is employed for the production of antibodies for use in immunoassays. The enzyme conjugate is employed as a reagent for the determination of nortriptyline in immunoassays. The antibodies and enzyme conjugates are provided in combination in kits to be used for the rapid and accurate determination of nortriptyline in serum as well as other physiological fluids.

DESCRIPTION OF THE PREFERRED EMBODIMENTS

Novel compounds are provided which are nortriptyline derivatives having a functionality at the 3-position to which is conjugated a poly(amino acid), which is antigenic or an enzyme. The antigenic conjugates are employed as an immunogen for the production of antibodies which are specific for nortriptyline; the antibodies find use in immunoassays. The enzyme conjugates are employed as a reagent in enzyme assays for the determination of nortriptyline.

For the most part, compounds of this invention will have the following formula:

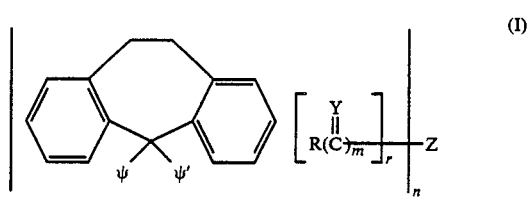

(I)

wherein:

$\Psi$ and $\Psi'$ may be taken together to form a double bond to an oxygen atom (oxo) or to a carbon atom substituted with G ($\Psi$ and $\Psi'$ therefore being =CH—G)

wherein G is an aliphatic group having from 4 to 8 atoms, other than hydrogen atoms, usually 5 to 6 atoms other than hydrogen atoms, which are carbon atoms and nitrogen atoms wherein nitrogen is amino, preferably tertiary amino, wherein G may be

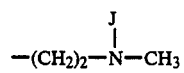

($\Psi$ and $\Psi'$ therefore being:

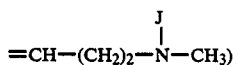

wherein J is a hydrogen atom, methyl, or non-oxo-carbonyl, usually alkoxy carbonyl of from 2 to 6 carbon atoms, preferably 3 to 4 carbon atoms, which may contain from 0 to 3 halogen atoms of atomic number 17 to 35, usually chlorine atoms, normally as $\beta$-substituents when three or more carbon atoms are present.

$\Psi$ and $\Psi'$, when taken separately, may be, respectively, oxy, usually hydroxy, and an aliphatic group of from 4 to 8 atoms other than hydrogen atoms usually 5 to 6 atoms other than hydrogen which are carbon and nitrogen, usually 4 to 5 carbon atoms and 0 to 1 nitrogen atoms wherein nitrogen is amino, preferably tertiary amino;

R is a bond or an aliphatic linking group of from 1 to 20 atoms other than hydrogen atoms, preferably 5 to 15 atoms other than hydrogen atoms, more preferably 7 to 12 atoms other than hydrogen atoms, which may be carbon atoms, nitrogen atoms, chalcogen (oxygen and sulfur atoms), including a chain of from 1 to 15 atoms other than hydrogen atoms, preferably from 3 to 12 atoms other than hydrogen atoms, more preferably from 5 to 10 atoms other than hydrogen atoms; usually from 1 to 10, preferably from 2 to 6, carbon atoms; usually from 0 to 5, preferably 1 to 3, oxygen atoms present as ox-carbonyl, non-oxo-carbonyl or ether, particularly non-oxo-carbonyl; usually from 0 to 3, preferably 1 to 2, nitrogen atoms present as amido, preferably having 1 nitrogen linked to the aromatic nucleus; and usually from 0 to 2 sulfur atoms present as thiono or disulfide; wherein for each carbon atom no more than one heteroatom is linked thereto through a saturated bond;

Z is amino (r is 0); a hydrogen atom, alkoxy (including sulfur analogs) of from 1 to 6 carbon atoms, usually 1 to 3 carbon atoms, where for sulfur analogs Z may be taken together with R to form a disulfide; or poly(amino acid) (PAA) which is antigenic or an enzyme;

m is 0 or 1, generally being 1 when Z is other than PAA;

r is 0 or 1, being 0 when Z is amino, and being otherwise 1;

n is 1 when Z is other than PAA and is otherwise a number on the average between 1 and the molecular weight of Z divided by 500, more usually divided by 1,000 and frequently divided by 1,500, generally ranging from 1 to 500, preferably from 10 to 100, when Z is an antigen, and from 1 to 30, more usually 2 to 20, and preferably from 2 to 16, when Z is an enzyme.

For those compounds where r is 0 and n is 1, the compounds will be of the following formula:

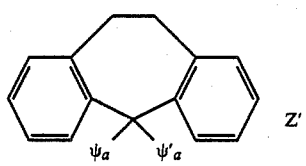

(II)

wherein:

$\Psi_a$, and $\Psi'_a$ may be taken together to form a double bond to an oxygen atom (oxo) or $\Psi_a$ and $\Psi'_a$ may be taken separately, respectively, as oxy and an aliphatic group of from 4 to 8 atoms other than hydrogen atoms, usually 5 to 6 atoms other than hydrogen atoms, which are carbon atoms and nitrogen atoms, usually 4 to 5 carbon atoms and 0 to 1 nitrogen atoms wherein nitrogen is amino, preferably tertiary amino; and Z' is amino.

For those compounds where m is 0 and r and n are 1 the compounds will generally be of the formula:

$$R^1-Z^2 \quad (III)$$

$\psi_b \; \psi_{b'}$ wherein:

$\Psi_b$ and $\Psi'_b$ may be taken together to form a double bond to carbon substituted with G ($\Psi$ and $\Psi'$ therefore being =C—G) wherein G is an aliphatic group having from 4 to 8 atoms other than hydrogen, usually 5 to 6 atoms other than hydrogen atoms, which are carbon atoms and nitrogen atoms wherein nitrogen is amino, preferably tertiary amino, wherein G may be

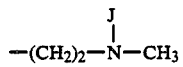

($\Psi$ and $\Psi'$ therefore being

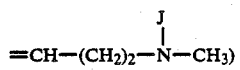

wherein J is a hydrogen atom, methyl, or non-oxo-carbonyl, usually alkoxy carbonyl of from 2 to 6 carbon atoms, preferably 3 to 4 carbon atoms, which may contain, from 0 to 3 halogen atoms of atomic number 17 to 35, usually chlorine atoms, normally as β-substituents when three or more carbon atoms are present:

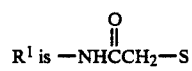

$Z^2$ is a hydrogen atom or alkyl thio of from about 1 to 6 carbon atoms, preferably 1 to 3 carbon atoms.

When $Z^2$ is a hydrogen atom taken together with $R^1$ to give thiol, the compounds may be stabilized as a salt,, e.g., an acetate salt.

When Z is a poly(amino acid), preferred compounds will for the most part have the formula:

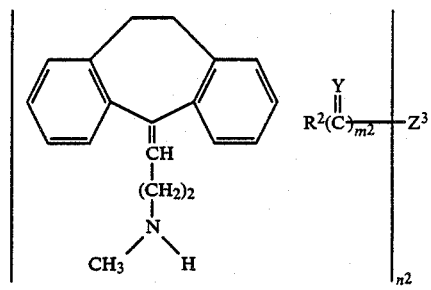

(IV)

wherein:

$R^2$ is $M(Q)_aTSD$, wherein D may be, e.g.,

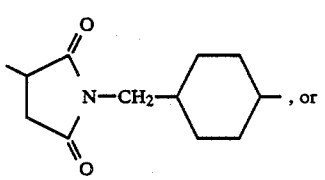

, or

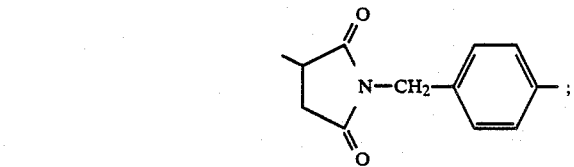

M is amino;

Q is C=W, wherein W is an oxygen atom, imino (N—H), or a sulfur atom, particularly an oxygen atom;

a is 0 or 1;

T and T' are linking groups of from 1 to 4, preferably 1 to 2, carbon atoms, preferably aliphatic, more preferably alkylene, particularly methylene; when a is 0, T must be at least two carbon atoms;

Y and Y' are independently an oxygen atom, imino (N—H), or sulfur atom, preferably an oxygen atom;

A is imino;

k is 0 or 1;

p is 0 or 1, preferably 1;

$m^2$ is 0 or 1, preferably 1;

$n^2$ is at least 1, and usually greater than 1; when $Z^3$ is antigenic, $n^2$ will normally be at least 2, and on the average not greater than the molecular weight of $Z^3$ divided by 500, usually not greater than the molecular weight of $Z^3$ divided by 1,000, and preferably not greater than the molecular weight of $Z^3$ divided by 1,500, generally ranging from about 2 to 500; when $Z^3$ is an enzyme, $n^2$ will be at least 1, usually not greater than 30, more usually in the range of about 2 to 20, and preferably in the range of about 2 to 16.

$Z^3$ is a poly(amino acid) and will generally range from about 5,000 molecular weight, having no upper molecular weight limit, normally being not less than 10,000, usually not more than about 600,000. There will usually be different molecular weight ranges, depending on whether an antigen or an enzyme is involved, with antigens ranging from about 5,000 to $10^7$, usually from about 20,000 to 600,000, and more usually from about 25,000 to 250,000 molecular weight; while enzymes will generally range from about 10,000 to 600,000 more usually from about 10,000 to 300,000 molecular weight. There will usually be at least about one conjugate group per 500,000 molecular weight, more usually at least one per 50,000 molecular weight. With intermediate molecular weight antigens (35,000 to 1,000,000), the number of conjugate groups will generally be from about 2 to 250, more usually from 10 to 100. With lower molecular weight antigens, below 35,000, the number of conjugate groups will generally be in the range of from about 2 to 10, usually in the range of 2 to 5.

The preferred compounds of the invention have the following formula:

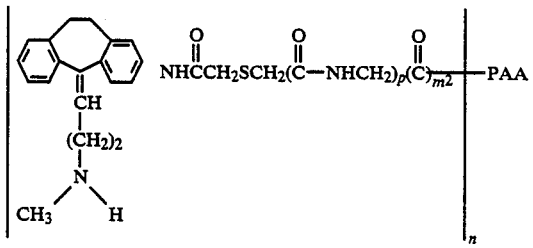

wherein:

p, $m^2$, and n have been defined previously and

PAA is poly(amino acid) which has been defined previously.

Various protein types may be employed as the poly(amino acid) antigenic material. These types include albumins, serum proteins, e.g., globulins, ocular lens proteins, lipoproteins, etc. Illustrative proteins include bovine serum albumin, keyhole limpet hemocyanin, egg ovalbumin, bovine γ-globulin, etc. Alternatively, synthetic poly(amino acids) may be prepared having a sufficient number of available amino groups, e.g., lysines.

The enzymes can be varied widely, depending upon the rapidity with which one desires a result and the physiological fluid in which the nortiptyline is to be measured. Primarily, the enzymes of choice, based on the I.U.B. classification are: Class 1. Oxidoreducatases and Class 3. Hydrolases. Particularly in Class 1, the enzymes of interest are dehydrogenases of Class 1.1, more particularly 1.1.1, 1.1.3, and 1.1.99 and peroxidases in Class 1.11. Of the hydrolases, particularly Class 3.1, more particularly 3.1.3 and Class 3.2, more particularly 3.2.1.

Illustrative dehydrogenases include malate dehydrogenase, glucose-6-phosphate dehydrogenase, and lactate dehydrogenase. Of the oxidases, glucose oxidase is exemplary. Of the peroxidases, horse radish peroxidase is illustrative. Of the hydrolases, alkaline phosphatase, β-galactosidase, β-glucosidase and lysozyme are illustrative.

Particularly preferred are those enzymes which employ nicotinamide adenine dinucleotide (NAD) or its phosphate (NADP) as a cofactor, particularly the former. Most preferred as the choice of enzyme is glucose-6-phosphate dehydrogenase.

Desirably the conjugated enzyme will be at least 40% inhibited, usually at least about 60% inhibited when saturated with anti(nortiptyline) while the conjugate will be less than 80% deactivated, preferably less than 60% deactivated, as compared to the native enzyme.

The synthetic scheme for preparing the subject compounds is set forth in the following flowchart:

Chart 1

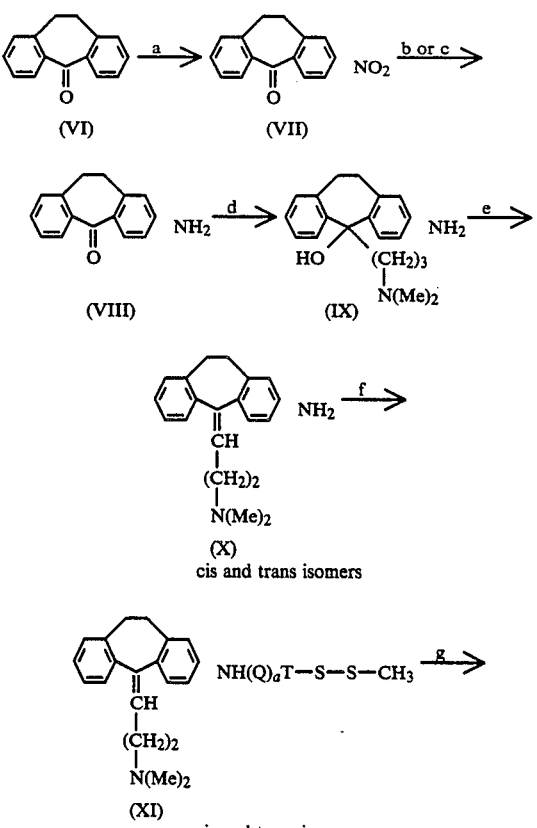

-continued

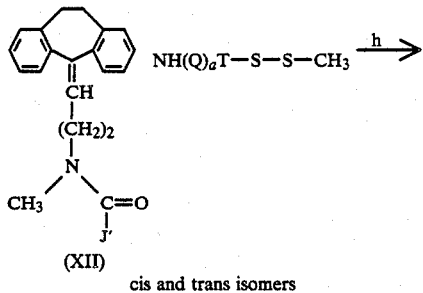

(XII)
cis and trans isomers

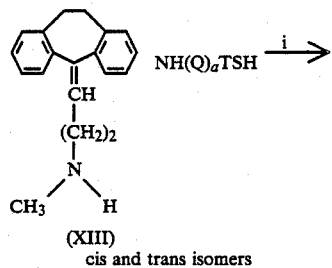

(XIII)
cis and trans isomers

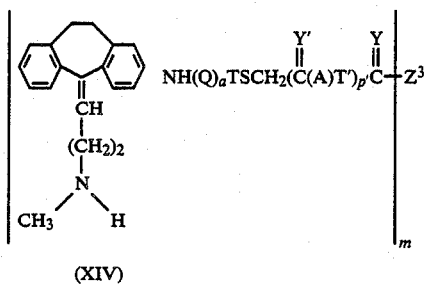

(XIV)

wherein X, $Y^1$, A, k, $T^1$, p, y, and $Z^3$ have been defined previously.

In carrying out the preparation of the compounds of the invention, dibenzosuberone VI is treated with a nitrating agent, preferably in equimolar amounts, to give 3-nitrodibenzosuberone VII. Reduction of VII is achieved by catalytic hydrogenation or with dithionite giving (VIII). Reaction of VIII with a Grignard reagent gave IX, which is dehydrated to yield X. XI is obtained from X by mixing X with an activated ester for linking to the amino group. XI is demethylated under mild alkaline conditions to give XII, which gave secondary amine XIII upon reduction. Poly(amino acid) conjugates (XIV) of XIII are prepared by combining XIII with the appropriate activated poly(amino acid) conjugate to combine with the sulfhydryl group of XIII, e.g., activated by the presence of a halogen atom or an olefinic bond.

By employing the above procedure conjugates of nortriptyline and poly(amino acids), either antigenic or enzymes, may be prepared. The structure of nortriptyline is present after the synthetic procedure and those elements of the structure which provide for distinctions between closely similar compounds are exposed to allow for formation of antibodies which are capable of distinguishing nortriptyline from similarly structured compounds. The antigenic compounds may be injected into a wide variety of vertebrates in accordance with conventional methods for the production of antibodies. Usually the animals are bled periodically with successive bleeds having improved titer and specificity, then reaching a maximum and diminishing in their specificity and titer. The antibodies prepared in accordance with the present invention are capable of binding with the above antigenic and enzyme conjugates specific for nortriptyline and are able to distinguish between closely related compounds and metabolites of nortriptyline such as amitriptyline and imipramine.

As previously indicated, the antibodies and enzyme reagents prepared in accordance with the subject invention find particular use in immunoassays for the determination of nortriptyline. A description of the method for carrying out the immunoassay, which is a homogeneous enzyme immunoassay, may be found in U.S. Pat. No. 3,817,837. The method involves combining the enzyme conjugate, the unknown sample (after treatment to remove metabolites by, e.g., chromatographic separation) suspected of containing nortriptyine, and an antibody for nortriptyline in an aqueous buffered medium at temperatures in the range of about 10° to 50° C., more usually from about 20° to 40° C., and determining the enzyme activity as compared to the enzyme activity of an assay medium having a known amount of nortiriptyline.

EXAMPLES

The following examples are offered by way of illustration and not by way of limitation.

All temperatures not otherwise indicated are in centigrade. All parts and percents are by weight except for mixture of liquids which are by volume.

tlc—thin layer chromatography;
GF—gel filtration;
IR—infrared spectroscopy;
$CDCl_3$—deuterated chloroform;
Pmr—proton magnetic resonance spectroscopy,
MHz—megahertz;
TMS—trimethylsilane;
M.S.—mass spectroscopy;
h—hour;
NHS—N-hydroxysuccinimide;
DMF—dimethylformamide;
EDCI—1-ethyl-3-(3-dimethylaminopropyl) carbodiimide hydrochloride;
BSA—bovine serum albumin;
RSA—rabbit serum albumin;
BgG—bovine gamma globulin;
G-6-PDH—glucose-6-phosphate dehydrogenase
G-6-P(Na)—glucose-6-phosphate sodium
BLG—$\beta$-lactoglobulin

EXAMPLE 1

Preparation of 3-nitrodibenzosuberone

Acetic anhydride (15 ml) was added slowly to white fuming nitric acid (90%, 6.1 ml, 0.13 mole) at room temperature. The resulting warm (30°) solution was cooled to 25° and was added dropwise to a solution of dibenzosuberone (20.8 g, 0.1 mole, from Aldrich Chemical Co.) in 25 ml of acetic anhydride at room temperature for a period of three hours. After addition, an aliquot was withdrawn, and quenched in water, and partitioned in dichloromethane; tlc showed the presence of 3-nitrodibenzosuberone, some fast moving substance, and starting material. The reaction mixture was then added to 2 liters of ice water and the oily product was stirred for half an hour. The resulting aqueous layer was decanted and discarded, and the oily residue on the bottom was dissolved in dichloromethane and washed with saturated sodium bicarbonate and brine. The organic layer was dried over MgSO$_4$ and evaporated to yield light yellow oil which was crystallized by dissolving in warm ether and adding hexane until cloudiness developed. The resulting clear solution was cooled (5°) overnight to yield 6.5 g of pale yellow solid (26% yield) of 3-nitrodibenzosuberone. The tlc of this material showed a major product and a small amount of impurity; the product was used without further purification.

Anal. Calcd. for C$_{15}$H$_{11}$NO$_3$, C, 71.15; H, 4.35; N, 5.53. Found: C, 69.42; H, 4.34; N, 5.85

EXAMPLE 2

Preparation of 3-aminodibenzosuberone

To a suspension of 3-nitrodibenzosuberone (27.2 g, 0.107 mole) from Example 1 in a mixture of tetrahydrofuran (800 ml), isopropanol (800 ml) and phosphate buffer [pH 6.5, 1.6 liters, prepared by mixing 13.6 g KH$_2$PO$_4$ (0.1 molar) and 27.8 ml of 1N NaOH and diluting the resulting solution to 2 liters] was added sodium dithionite (220 g, from Eastman Organic Chemicals) over a period of 5 min. The solids became soluble, and after 15 min. tlc showed complete reaction. The resulting clear solution was then extracted exhaustively with ethyl acetate and the organic layer was washed with saturated NaCl solution, and dried over Na$_2$SO$_4$. Evaporation of solvents gave yellow crude product which was chromatographed on a silica gel column and eluted with ether/hexane 1:1 to yield 8.7 g (36% yield) pure yellow 3-aminodibenzosuberone.

EXAMPLE 3

Preparation of 3-amino-5-(3-dimethylaminopropyl)-5-hydroxy-10,11-dihydrodibenzo[b,e]cycloheptatriene a. Preparation of N,N-dimethylpropylchloride A solution of N,N-dimethylpropyl chloride hydrochloride (100 g, from Aldrich Chemical Co.) in about 100 ml water was made alkaline by adding 10% NaOH to pH of about 11-12. The resulting bi-layer solution was then extracted with ether, and the ether extracts were dried over MgSO$_4$. Then, the ether was distilled using a simple distillation apparatus under 1 atm pressure, and the resulting liquid was distilled at 45° (60 mm pressure) to yield 54.5 g colorless liquid of N,N-dimethylpropyl chloride.

b. Grignard reaction:

To Mg turnings (13 g., 0.54 mole) in tetrahydrofuran (53 ml, dried and distilled freshly over the sodium salt of benzophenone) was added a few drops of 1,2-dibromoethane (J. T. Baker Chemical Co.) under nitrogen. After crushing the turnings with a glass rod and noting gas evolution, a solution of N,N-dimethylpropyl chloride (32.3 g, 0.27 mole) in tetrahydrofuran (150 ml) was added dropwise. During this addition the solution was heated sufficiently to maintain a gentle reflux. After stirring for 1 h under reflux, the brown reaction mixture was cooled to room temperature followed by addition of 3-aminodibenzosuberone (12.4 g, 0.056 mole) from Example 2 in dry THF (220 ml). The resulting brown product was allowed to stir at room temperature for half an hour and was cautiously quenched with saturated ammonium chloride (200 ml). The resulting yellow residue was extracted with ethyl acetate. The organic phase was washed with saturated NaHCO$_3$ and brine, dried (Na$_2$SO$_4$), and evaporated to yield a yellow oil (17.2 g) of 3-amino-5-(3-dimethylaminopropyl) 5-hydroxy-10,11-dihydrodibenzo[b,e]cycloheptatriene.

EXAMPLE 4

Preparation of 3-aminoamitriptyline

To a solution of 3-amino-5-(3-dimethylaminopropyl)-5-hydroxy-10,11-dihydrodibenzo[b,e]cycloheptatriene (17.1 g, 0.055 mole) from Example 3 in dichloromethane (300 ml) was added trifluoroacetic acid (29.6 ml, 0.175 mole). The resulting dark brown solution was refluxed for 18 hours; tlc of an aliquot of the reaction mixture showed incomplete reaction. Therefore, p-toluenesulfonic acid monohydrate (10.5 g, 0.055 mole) was added and refluxed overnight. After 18 hours, complete reaction was observed. The reaction product was cooled, diluted with ether, made alkaline with concentrated ammonia (22 ml), and then extracted with ethyl acetate. Evaporation of solvents gave a foaming product containing two major components and some impurities of higher Rf values. The samples were purified using preparative HPLC (silica gel column, NH$_3$:MeOH:CH$_2$Cl$_2$/0.24:3:97 by volume):

Fractions were collected and analyzed using both refractive index and analytical tlc (silica gel plate, 0.08:1:7/NH$_3$:MeOH:CH$_2$Cl$_2$). Fractions of the same Rf values were combined and evaporated to give 6.8 g cis-3-aminoamitriptyline Rf 0.08 and 3.6 g trans 3-aminoamitriptyline Rf 0.15. Total yield of the products from 3-aminodibenzosuberone over two steps is 10.4 g (64% yield). Anal. calcd. for cis 3-aminoamitriptyline, C$_{20}$H$_{24}$N$_2\frac{1}{2}$H$_2$O, C, 79.73; H, 8.31; N, 9.30. Found, C, 79.53; H, 7.99; N, 8.89.

EXAMPLE 5

Preparation of cis-N'-(methyldithioacetyl)-3-aminoamitriptyline

To a solution of cis-3-aminoamitriptyline (2.7 g, 9.3 mmole) from Example 4 in a mixture of tetrahydrofuran (80 ml, dried and distilled freshly from sodium benzophenolate) and dichloromethane (20 ml, dried over molecular sieves 3A) was added the NHS ester of methyldithioacetic acid (2.9 g, 13.8 mmole). The resulting solution was allowed to stir at room temperature. After four days, complete reaction was observed on tlc. The resulting light yellow solution was evaporated to dryness on a rotary evaporator and the residue was chromatographed on a reversed phase silica gel column [containing 300 g silica gel 60 silanized], and eluted with 3% MeOH/CH$_2$Cl$_2$ (1.4 liter) and then 5% MeOH/CH$_2$Cl$_2$ (600 ml). After evaporation of solvents, 4.3 g light yellow foaming product, which contained the cis-N'-methyl(dithioacetyl)3-aminoamitriptyline was obtained. The product was dissolved in 100 ml of CH$_2$Cl$_2$, and 1 ml triethylamine was added. The organic layer was washed with saturated NaCl and dried over Na$_2$SO$_4$, and evaporated to yield 3.3 g (86% yield) foaming product of cis-N'-methyl(dithioacetyl)3-aminoamitriptyline.

EXAMPLE 6

Preparation of cis-N($\beta,\beta,\beta$-trichloroethoxycarbonyl)-N-methyl(dithioacetyl)-3-aminonortriptyline To a solution of cis-N'-(dithioacetyl)-3-aminoamitriptyline (3 g, 7 mmole) from Example 5 in dichloromethane (120 ml, dried over molecular sieves 3A) was added trichloethyl chloroformate (9.6 ml, 70 mmoles) dropwise at room temperature under nitrogen atmosphere followed by triethylamine (9.7 ml, 70 mmoles) for a period of 15 min. The slightly warm reaction mixture was cooled using a water bath and then allowed to stand at room temperature for 3.5 h. Complete reaction was obtained as observed on analytical silica gel plates. The resulting yellow solution was evaporated to dryness. Ether (100 ml) was added; white precipitates which formed were filtered and then washed with ether. The ether filtrates were collected and evaporated to yield a brown oil which was chromatographed on silica gel. Fractions were analyzed by tlc and detected using both UV and $I_2$ since the product showed a UV chromophore, while the impurities had no UV absorption but showed brown spots of higher Rf values when being developed in an $I_2$ chamber. Fractions were combined to give (3.2 g, 77% yield) cis-N-($\beta,\beta,\beta$-trichloroethoxycarbonyl) 3-amino-N'-(methyldithioacetyl) nortriptyline as a white foaming product. Fractions containing impurities were either chromatographed again or discarded since the impurities interfered with the reductive cleavage of the methyldithioacetyl derivative in the next reaction. The sample after column chromatography showed the correct structure.

Anal. calcd. for $C_{25}H_{27}N_2O_3Cl_3S_2$ C, 52.31; H, 4.71; N, 4.88; Cl, 18.57 S, 11.16. Found: C, 52.41; H, 4.85; N, 4.73; Cl, 18.14; S, 10.84.

EXAMPLE 7

Preparation of cis-3-amino-N'-(mercaptoacetyl) nortriptyline

All solutions used in work up of the sulfhydryl derivative were degassed by bubbling argon through each solution at room temperature for at least 10 min.

To a solution of cis-N-($\beta,\beta,\beta$,-trichloroethoxycarbonyl)-3-amino-N'-(methyldithioacetyl) nortriptyline (500 mg, 0.87 mmole) from Example 6 in glacial acetic acid (10 ml) was added activated zinc dust (1.5 g) at room temperature under nitrogen. The zinc dust was activated by washing well with 100 ml of 2% HCl for 4–5 min, then filtered and zinc powder was washed with water, ethyl alcohol, acetone and dry ether. The powder was then dried overnight at reduced pressure at room temperature and then used for reduction. The reaction mixture was allowed to stir overnight at room temperature. After 22 hours, the reaction mixture was filtered and washed with about 40 ml of water, and the filtrate was cooled in an ice bath. White precipitates (Rf 0.95, 114 mg) formed and were removed by filtration and discarded, and the filtrate was extracted with 2×10 ml ether/hexane (1:1), or until the complete removal of side product. The resulting aqueous solution was then extracted with a total of 200 ml dichloromethane and the organic solution washed with brine and dried over $Na_2SO_4$. Evaporation of solvents gave a clear viscous oil of the acetate of cis 3-amino-N'-(mercaptoacetyl) nortriptyline (104 mg, 29% yield, Rf 0.31).

The product was found to be decomposed under vacuo at room temperature within a day. However, under acidic conditions, e.g., the acetate salt, the product was found to be more stable. The acetate salt of 3-amino-N'-(mercaptoacetyl) nortriptyline was stored under nitrogen, or argon, and kept at dry ice temperature.

EXAMPLE 8

Preparation of the Conjugate of Cis-3-amino-N'-(mercaptoacetyl) Nortriptyline and Bromoacetylglycyl BgG a. Preparation of the NHS ester of bromoacetylglycine To a solution of bromoacetylglycine (1 g, mp. 114°–115°) in 10 ml of DMF was added powdered NHS (1 g) and EDCI (1 g, 5.2 mmole) under nitrogen at 0°. The resulting clear solution was then allowed to stir at 5° after 18 h and used directly without the isolation of the NHS ester.

b. Conjugation of bromoacetylglycine to BgG

To a clear solution of BgG (1.5 g) in a mixture of phosphate buffer (100 ml, pH 9, 0.05M) and DMF (5 ml) was added dropwise the NHS ester of bromoacetylglycine (500 mg in 6 ml DMF, prepared as above) at 0° for a period of 30 min. The pH of the BgG solution before the addition of NHS solution was 8. The pH dropped to 6.3 after addition of the NHS solution; the pH was then adjusted to 6.8. The resulting mixture was allowed to stir overnight at 5°. After 18 hours, the conjugate was dialyzed against 4×4 liter phosphate buffer (0.0125M, pH 6.8) 2×4 liter (0.05M, pH 6.8). The conjugate was diluted to 150 ml and stored for further conjugation. The concentration of this protein conjugate was determined by UV and found to be 9.58 mg/ml.

c. Conjugation of cis-3-amino-N'-(mercaptoacetyl) nortriptyline to bromoacetylglycyl BgG To the bromoacetylglycyl BgG solution (212 mg) prepared as above in 30 ml of 0.1 m phosphate buffer (pH 7, pre-degassed with nitrogen) was added cis-3-amino-N'-(mercaptoacetyl) nortriptyline acetate (35 mg in 1.75 ml DMF) prepared as in Example 7. The resulting cloudy solution was kept under nitrogen at 5° for 70 hours. The milky solution was then dialyzed against 2×4 liter $NH_4OH—H_2O$, pH 9, 2×1 liter 8M urea, 1 liter 4M urea, 1 liter 2M urea and then 5×4 liter $NH_4OH—H_2O$, pH 9. The pH of the conjugate was adjusted to 10 with 15% $NH_4OH$ and centrifuged at 3K, 10 min. Supernatant was lyophilized to give a conjugate (205 mg) of hapten number 46.

EXAMPLE 9

Preparation of the Conjugate of Cis-3-amino-N'-(mercaptoacetyl) Nortriptyline and Bromoacetylglycyl BSA a. Preparation of conjugate of bromoacetylglycine to BSA To a clear solution of BSA (1.5 g) in phosphate buffer (pH 9.0, 0.05M, 100 ml) and DMF (6 ml) was added dropwise the NHS ester of bromacetylglycine (500 mg), in 6 ml DMF at 0° for a period of 30 min. Before the addition of the NHS ester, the pH of the BSA solution was about 8.0. After the addition of the NHS ester, the pH dropped to 5–6; the pH (5.86) of the reaction mixture was adjusted to 6.8 and stirred overnight at 5°. The resulting conjugate was then dialyzed against 3×4 liter phosphate buffer (0.0125M, pH 6.8) and 2×4 liter phosphate buffer (0.05M, pH 6.8). The conjugate was diluted to 150 ml and stored for further conjugation. The concentration of this protein conjugate was determined by UV and found to be 8.8 mg protein/ml solution.

b. Conjugation of cis-3-amino-N'-(mercaptoacetyl) nortriptyline to bromoacetylglycyl BSA To the bromoacetylglycyl BSA (250 mg) prepared as above in a mixture of phosphate buffer (41 ml. pH 7) and DMF (8 ml), [the solutions used for conjugation were saturated with nitrogen gas] was added cis-3-amino-N'-(mercaptoacetyl) nortriptyline free base (65 mg, prepared as in Example 7) in 3 ml of DMF. The resulting mixture was then stirred under nitrogen at 5° for a total of 72 hours and dialyzed exhaustively against $NH_4OH/H_2O$ (10×4 l). The conjugate was then lyophilized to give 194 mg protein (hapten number 24).

EXAMPLE 10

Preparation of the Conjugate of trans-3-Amino-N'-(mercaptoacetyl)nortriptyline and Bromacetylglycyl G-6-PDH (a) Preparation of conjugate of bromoacetylglycine (BAG) and G-6-PDH The above BAG/G-6-PDH conjugate was prepared according to the procedure disclosed in U.S. Pat. No. 4,220,722 at columns 18–19 (the disclosure of which is incorporated herein by reference). The conjugate was dialyzed against 4 l of tris buffer without preservatives (0.05% azide 0.005% Thimerasol) to give 13.8 mg of conjugate in 6.1 ml.

(b) Conjugation of trans-3-amino-N'-(mercaptoacetyl)nortriptyline to bromoacetylglycyl G-6-PDH A solution of 19 mg trans-3-amino-N'-(mercaptoacetyl) nortriptyline from Example 7 in 0.5 ml of DMF containing 50 μl of glacial acetic acid was prepared. This solution (125 μl) was degassed with argon and was added to the 6.1 ml of the dialyzed BAG/G-6-PDH from above. The resulting mixture was stirred for 3.5 h at 4° and then centrifuged. The supernatant was chromatographed on a Sephadex G-50 column and fractions containing protein were collected. The product was 84% deactivated and 40% inhibitable.

EXAMPLE 11

Preparation of the Conjugate of G-6-PDH and 5-(3-N-Methylaminopropyl)-10,11-dihydro-10-thioacetamido-5H-dibenz[b,f]azepine a. Preparation of the conjugate of bromoacetyl glycine and G-6-PDH (61 mg) with 8 ml of 0.055M tris buffer at pH 3.0) was brought to 4° and 320 mg each of G-6-P($Na_2$) salt and NADH were added and dissolved. To this solution a 0.5M bromoacetylglycyl NHS ester in DMF, prepared as in Example 10 above, was added slowly with stirring until the deactivation of the enzyme was 65%. The solution was dialyzed against tris buffer (0.055M, pH 8.0, 4000 ml) for 18 h.

b. Conjugation of 5-(3-N-methylaminopropyl)-10,11-dihydro-10-thioacetamido-5H-dibenz[b,f]azepine to bromoacetylglycyl G-6-PDH The hapten material (63 mg) from Example 5 was reconstituted in 1.5 ml DMF. All of the dialyzed material from Example 9 was placed inside a flask and cooled to 4°. The hapten was added dropwise until the inhibition against anti-DMI antibodies was 45–50% (a hapten to enzyme ratio of about 95). The G-6-PDH conjugate was then desalted at 4° over a G50 column with tris buffer (0.055M, pH 8.0) with preservatives.

EXAMPLE 12

Assay for Nortriptyline

In order to demonstrate the efficacy of compounds prepared in accordance with the subject invention, antibodies produced in the conventional manner in response to the conjugate of Example 8 and the enzyme conjugates prepared in Example 11 were employed in a number of assays for nortriptyline. In carrying out the assay, a Gilford 300N microsample spectrophotometer was employed with a Thermocuvette with a flow cell. All readings were made at 340 mn. The following solutions were prepared as reagents for use in the assay.

Buffer:
0.055M tris-HCl pH 8.1 (RT)
Enzyme Conjugate from Example 11b:
Buffer
0.9% NaCl
1.0% BLG, pH 8.1 (RT)
Sufficient enzyme conjugate from Example 11 to give a maximum rate of ΔOD equal to 700–1000 in the assay medium
Assay buffer:
Buffer
0.5% NaCl
0.01% (v/v Triton X-100, pH 8.1 (RT)
Antibody Reagent:
Buffer
0.1% BLG,
G-6-P(Na) 0.198M,
NAD 0.2M, pH5 (RT)
Antinortriptyline optimized for assay (antibodies prepared in sheep using the conjugate of Example 9)
All % indicated are w/v, g/ml.

The protocol employed for carrying out an assay was as follows:

The sample was treated first to remove metabolites. A 100 mg C-2 column was washed with approximately one ml of methanol followed by approximately one ml of water. The sample (500 μl) was placed on the top of the column. A vacuum apparatus was attached to the bottom and a vacuum was drawn on the column. The eluate obtained was discarded and the column was washed with 900 μl of a solution which was 70% 0.1M sodium acetate, pH 4.2, 30% acetonitrile, and 5 mM heptane sulfonate. A vacuum was again drawn on the column and the eluate was discarded. Next, the column was contacted with 500 μl of a solution which was 50% acetonitrile, 25% methanol, and 25% 5 mM $K_2HPO_4$, pH 7. The eluant was collected and used in the assay procedure.

Into a diluter was drawn 15 microliters (μl) of the above sample. The sample was dispensed with 250 microliters of the assay buffer into a one milliliter Croan cup. Into the Croan cup was introduced 15 μl of the antibody reagent with 250 μl of the assay buffer, followed by the addition of 15 μl of the enzyme reagent and 250 μl of the assay buffer. Immediately after the enzyme addition, the entire sample was aspirated into the flow cell. After 10 seconds, a first reading was taken, followed by a second reading after a 50 second interval. The results are reported as the difference in absorbance X 2.667.

| Sample Concentration of Nortriptyline (ng/ml) | ΔOD |
| --- | --- |
| 0 | 695 |
| 25 | 723 |
| 50 | 761 |
| 100 | 807 |
| 175 | 850 |
| 250 | 870 |

The subject assay provides for a sensitive accurate method for determining nortriptyline in biological fluids such as serum. The subject invention provides reagents specific for nortriptyline, which allows for a substantial range of changes in enzyme activity with change in concentration of nortriptyline. The method is rapid, the protocol is simple and relatively free of technician introduced error and can be performed substantially in the same manner as an enzyme assay.

Although the foregoing invention has been described in some detail by way of illustration and example for purposes of clarity and understanding, it will be obvious that certain changes or modifications may be practiced within the scope of the appended claims.

What is claimed is:
1. A compound of the formula

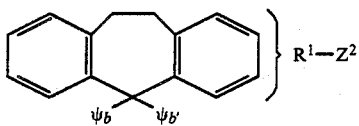

wherein:
$\Psi_b$ and $\Psi_{b'}$ may be taken together to form a double bond to carbon substituted with G, wherein G is an aliphatic group having from 4 to 8 atoms other than hydrogen which are carbon and nitrogen wherein nitrogen is amino;

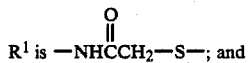

$R^1$ is $-NHCCH_2-S-$; and $Z^2$ is hydrogen or thio substituted with alkyl of from about 1 to 6 carbon atoms.

2. The compound of claim 1 wherein G is

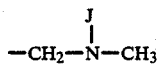

wherein J is methyl or alkoxy carbonyl of from 2 to 6 carbon atoms.

* * * * *